(12) United States Patent
Mauger

(10) Patent No.: US 11,589,872 B2
(45) Date of Patent: Feb. 28, 2023

(54) VASCULAR OCCLUSION DEVICES UTILIZING THIN FILM NITINOL FOILS

(71) Applicant: Nanostructures, Inc., Santa Clara, CA (US)

(72) Inventor: Philip Mauger, Santa Clara, CA (US)

(73) Assignee: Nanostructures, Inc., Santa Clara, CA (US)

(*) Notice: Subject to any disclaimer, the term of this patent is extended or adjusted under 35 U.S.C. 154(b) by 0 days.

(21) Appl. No.: 16/965,919

(22) PCT Filed: Jan. 29, 2019

(86) PCT No.: PCT/US2019/015716
§ 371 (c)(1),
(2) Date: Jul. 29, 2020

(87) PCT Pub. No.: WO2019/152434
PCT Pub. Date: Aug. 8, 2019

(65) Prior Publication Data
US 2021/0052278 A1 Feb. 25, 2021

Related U.S. Application Data

(60) Provisional application No. 62/624,672, filed on Jan. 31, 2018.

(51) Int. Cl.
*A61B 17/12* (2006.01)
(52) U.S. Cl.
CPC .. *A61B 17/12113* (2013.01); *A61B 17/12031* (2013.01); *A61B 17/12172* (2013.01)

(58) Field of Classification Search
CPC ........ A61B 17/12113; A61B 17/12031; A61B 17/12172; A61B 17/1214; A61B 17/12;
(Continued)

(56) References Cited

U.S. PATENT DOCUMENTS

| 5,263,964 A | 11/1993 | Purdy |
| 5,304,195 A | 4/1994 | Twyford et al. |

(Continued)

FOREIGN PATENT DOCUMENTS

| CN | 102202585 | 9/2011 |
| CN | 105142545 | 12/2015 |

(Continued)

OTHER PUBLICATIONS

International Sear Report and Written Opinion of International Application No. PCT/US2019/015716, dated May 16, 2019 in 12 pages.

(Continued)

*Primary Examiner* — Darwin P Erezo
*Assistant Examiner* — Raihan R Khandker
(74) *Attorney, Agent, or Firm* — Knobbe Martens Olson & Bear, LLP

(57) ABSTRACT

A deployable occlusion device for filling an aneurysm. The occlusion device includes a support structure, for example a wire or otherwise elongate structure. The occlusion device also includes a mesh component having a porosity. The mesh component has a first end portion and a second end portion. The first end portion of the mesh component is attached to the support structure and the second end portion of the mesh component is a free end. The mesh component extends from the support structure.

19 Claims, 11 Drawing Sheets

(58) Field of Classification Search
CPC ........... A61B 2017/00867; A61B 2017/00597;
A61B 2017/12054; A61B 17/12099;
A61B 17/12109; A61B 17/12122; A61B
17/0057; A61B 2017/00575–00632; A61L
31/02; A61F 2/86; A61F 2230/0067;
A61F 2230/0058; A61F 2/01; A61F
2/0105; A61F 2/011; A61F 2/012; A61F
2/013; A61F 2002/016; A61F 2002/018
USPC ........................................................ 606/200
See application file for complete search history.

(56) References Cited

U.S. PATENT DOCUMENTS

| | | | |
|---|---|---|---|
| 5,350,397 | A | 9/1994 | Palermo et al. |
| 5,624,449 | A | 4/1997 | Pham et al. |
| 5,749,894 | A | 5/1998 | Engelson |
| 5,928,260 | A | 7/1999 | Chin et al. |
| 5,980,514 | A | 11/1999 | Kupiecki et al. |
| 6,036,720 | A | 3/2000 | Abrams et al. |
| 6,077,291 | A | 6/2000 | Das |
| 6,168,622 | B1 | 1/2001 | Mazzocchi |
| 6,689,141 | B2 | 2/2004 | Ferrera et al. |
| 6,746,468 | B1 | 6/2004 | Sepetka et al. |
| 6,911,037 | B2 | 5/2005 | Gainor et al. |
| 7,011,094 | B2 | 3/2006 | Rapacki et al. |
| 8,142,456 | B2 | 3/2012 | Rosqueta et al. |
| 8,444,668 | B2 | 5/2013 | Jones et al. |
| 2001/0044634 | A1* | 11/2001 | Don Michael .......... A61F 2/012 606/200 |
| 2002/0026211 | A1* | 2/2002 | Khosravi ................. A61F 2/012 606/200 |
| 2003/0093097 | A1* | 5/2003 | Avellanet .......... A61B 17/12022 606/157 |
| 2003/0171739 | A1 | 9/2003 | Murphy et al. |
| 2003/0187475 | A1* | 10/2003 | Tsugita ................... A61F 2/013 606/200 |
| 2004/0087998 | A1 | 5/2004 | Lee et al. |
| 2004/0153025 | A1* | 8/2004 | Seifert ............. A61B 17/12113 604/19 |
| 2004/0193206 | A1 | 9/2004 | Gerberding et al. |
| 2005/0277978 | A1 | 12/2005 | Greenhalgh |
| 2007/0088387 | A1 | 4/2007 | Eskridge et al. |
| 2007/0191884 | A1 | 8/2007 | Eskridge et al. |
| 2007/0265656 | A1* | 11/2007 | Amplatz .......... A61B 17/12122 606/200 |
| 2007/0270902 | A1 | 11/2007 | Slazas et al. |
| 2009/0112228 | A1* | 4/2009 | Deshpande ....... A61B 17/22031 606/128 |
| 2009/0112249 | A1* | 4/2009 | Miles ................. A61B 17/1214 606/192 |
| 2009/0112251 | A1* | 4/2009 | Qian ................ A61B 17/12163 606/194 |
| 2009/0112253 | A1* | 4/2009 | Neilan ..................... A61F 2/013 606/200 |
| 2010/0094335 | A1 | 4/2010 | Gerberding et al. |
| 2011/0319926 | A1 | 12/2011 | Becking et al. |
| 2012/0065667 | A1* | 3/2012 | Javois .............. A61B 17/12172 606/213 |
| 2012/0095500 | A1* | 4/2012 | Heuser ................... A61F 2/0105 606/200 |
| 2012/0330341 | A1 | 12/2012 | Becking et al. |
| 2013/0116722 | A1 | 5/2013 | Aboytes et al. |
| 2013/0325053 | A1 | 12/2013 | Porter |
| 2014/0288633 | A1 | 9/2014 | Burke et al. |
| 2015/0216534 | A1 | 8/2015 | Riina et al. |
| 2015/0272590 | A1 | 10/2015 | Aboytes et al. |
| 2015/0297240 | A1 | 10/2015 | Divino et al. |
| 2015/0374483 | A1 | 12/2015 | Janardhan et al. |
| 2016/0022275 | A1 | 1/2016 | Garza |
| 2016/0022445 | A1 | 1/2016 | Ruvalcaba et al. |
| 2016/0051263 | A1 | 2/2016 | Morsi |
| 2016/0120551 | A1 | 5/2016 | Connor |
| 2016/0166257 | A1 | 6/2016 | Wayne et al. |
| 2016/0220265 | A1* | 8/2016 | Pokorney ............. A61B 17/221 |
| 2016/0324668 | A1 | 11/2016 | Wallace et al. |
| 2016/0374690 | A9 | 12/2016 | Connor |
| 2017/0027552 | A1* | 2/2017 | Turkington ...... A61B 17/12172 |
| 2017/0128077 | A1 | 5/2017 | Hewitt et al. |
| 2017/0143359 | A1* | 5/2017 | Nguyen .................. A61F 2/013 |
| 2017/0156734 | A1* | 6/2017 | Griffin ............ A61B 17/12172 |
| 2017/0165046 | A1* | 6/2017 | Johnson ................ A61F 2/0077 |
| 2017/0189035 | A1 | 7/2017 | Porter |
| 2017/0367710 | A1* | 12/2017 | Yang ............... A61B 17/12109 |
| 2017/0367713 | A1* | 12/2017 | Greene, Jr. ...... A61B 17/12109 |
| 2018/0098777 | A1* | 4/2018 | Gabbay ................. A61B 17/22 |
| 2018/0103971 | A1* | 4/2018 | Imai ............... A61B 17/320758 |
| 2018/0147041 | A1* | 5/2018 | Chouinard ............. A61F 2/013 |
| 2018/0153674 | A1* | 6/2018 | Walzman ................ A61F 2/962 |
| 2018/0206850 | A1* | 7/2018 | Wang ................... A61B 17/12 |
| 2018/0296224 | A1 | 10/2018 | Kealey et al. |
| 2018/0311029 | A1* | 11/2018 | Hocking ................. A61F 2/012 |
| 2019/0046343 | A1* | 2/2019 | Choubey .................. A61F 2/88 |
| 2019/0142435 | A1* | 5/2019 | DeMeritt .......... A61B 17/1214 606/191 |
| 2019/0223876 | A1* | 7/2019 | Badruddin ....... A61B 17/12031 |
| 2019/0343664 | A1 | 11/2019 | Ruvalcaba et al. |
| 2020/0323539 | A1 | 10/2020 | Mauger |
| 2021/0275189 | A9 | 9/2021 | Mauger |

FOREIGN PATENT DOCUMENTS

| | | |
|---|---|---|
| CN | 105142546 | 12/2015 |
| CN | 111936063 | 11/2020 |
| EP | 2932921 | 10/2015 |
| EP | 3745965 | 12/2020 |
| JP | 2017516605 | 6/2017 |
| WO | WO 2010/28314 | 3/2010 |
| WO | WO 2013/103888 | 7/2013 |
| WO | WO 2013/142756 | 9/2013 |
| WO | WO 2014/144980 | 9/2014 |
| WO | WO 2016/137997 | 9/2016 |
| WO | WO-2017106567 A1 * | 6/2017 ....... A61B 17/12113 |
| WO | WO 2017/205617 | 11/2017 |
| WO | WO 2019/152434 | 8/2019 |

OTHER PUBLICATIONS

International Search Report and Written Opinion issued in PCT Application No. PCT/US2017/034460, dated Aug. 29, 2017, in 16 Pages.

* cited by examiner

VASCULAR OCCLUSION DEVICES UTILIZING THIN FILM NITINOL FOILS

BACKGROUND

Field

This application is related to the methods and devices for treating neurovascular aneurysms.

Description of the Related Art

The worldwide occurrence of stroke is estimated to be in the vicinity of 60,000,00 instances per year. The economic and social costs for strokes are enormous. While most strokes are fatal or debilitating, even mild strokes often result in impairment that greatly diminishes quality of life and independence while substantially increasing direct costs for healthcare and daily living. Further, indirect costs such as lost productivity, expanded burden on care provided by immediate family, and the allocation of limited resources to rehabilitative therapy and convalescence aggregate to create a significant unmet need for the prevention of stroke beyond the current standard of care.

While advances in medical science, standards of care, preventative actions, and an understanding of the influences of personal lifestyle have improved in the field of stroke over time, the causes of stroke are complex and not fully understood in all instances. Stroke is divided into two categories: ischemic (loss of normal blood flow) and hemorrhagic (bleeding through blood vessel rupture).

A brain (cerebral) aneurysm is a bulging, weak area in the wall of an artery that supplies blood to the brain. If a brain aneurysm ruptures (a subarachnoid hemorrhage), it releases blood into the skull resulting in stroke. Depending on the severity of the hemorrhage, brain damage or death may result.

The risk factors for formation of aneurysms are recognized to include genetics, gender, age, race, elevated blood pressure, smoking, and atherosclerosis. In many cases an unruptured cerebral aneurysm may only be discovered during tests for another, usually unrelated, condition. In other cases, an unruptured cerebral aneurysm will cause problems by pressing on areas in the brain. When this happens, the person may suffer from severe headaches, blurred vision, changes in speech, and neck pain, depending on what areas of the brain are affected and how severe the aneurysm is.

An estimated 6 million people in the United States have an unruptured brain aneurysm, or 1 in 50 people. The annual rate of rupture is approximately 8-10 per 100,000 people or about 30,000 people per year in the United States who suffer a brain aneurysm rupture. There is a brain aneurysm rupturing every 18 minutes. Ruptured brain aneurysms are fatal in about 40% of cases. Of those who survive, about 66% suffer some permanent neurological deficit.

SUMMARY

At present there are three treatment options for people with the diagnosis of cerebral aneurysm: (1) medical (non-surgical) therapy; (2) surgical therapy or clipping; and (3) endovascular therapy or coiling.

Medical therapy is usually only an option for the treatment of unruptured intracranial aneurysms. Strategies include smoking cessation and blood pressure control. These are the only factors that have been shown to have a significant effect on aneurysm formation, growth, and rupture. Periodic radiographic imaging may be used to monitor the size and growth of an aneurysm. However, because the mechanisms of aneurysm rupture are not entirely understood, and because even aneurysms of very small size may rupture, monitoring cerebral aneurysms is an incomplete solution to meeting medical needs.

Surgical treatment of cerebral aneurysms has existed for more than 150 years, and for more than 80 years the standard of care has included the use of aneurysm clips which have evolved into hundreds of varieties, shapes, and sizes. The mechanical sophistication of available clips, along with the advent of the operating microscope in the 1960s have made surgical clipping the gold standard in the treatment of both ruptured and unruptured cerebral aneurysms.

Surgical clipping remains an invasive and technically challenging procedure whereby the brain and the blood vessels are accessed through an opening in the skull. After the aneurysm is identified, it is carefully separated from the surrounding brain tissue. A small metal clip is then secured to the base of the aneurysm. The choice of a. particular clip configuration is based on the size and location of an aneurysm. The clip has a spring mechanism which allows the clip to close around either side of the aneurysm, thus occluding the aneurysm from the blood vessel. Normal blood vessel anatomy is physically restored by excluding the aneurysm sac from the cerebral circulation.

Endovascular techniques for treating aneurysms date back to the 1970s with the introduction of proximal balloon occlusion. Guido Guglielmi an American-based neuroradiologist, invented the platinum detachable microcoil, which was used to treat the first human being in 1991.

Endovascualrly delivered coils are soft wire spirals originally made out of platinum. These coils are deployed into an aneurysm via a microcatheter that is inserted through the femoral artery of the leg and carefully advanced into the brain. The microcatheter is advanced into the aneurysm itself, and the microcoils are released in a sequential manner Once the coils are released into the aneurysm, the blood flow pattern within the aneurysm is significantly reduced, leading to thrombosis (clotting) of the aneurysm. A thrombosed aneurysm resists the entry of liquid blood, providing a seal in a manner similar to a clip.

Endovascular coiling is an attractive option for treating aneurysms because it does not require opening of the skull, and is generally accomplished in a shorter timeframe, which lessens the impact of physical strain on the patient. A limitation of coiling is that eventual compression of the bolus of individual coils may occur over time and thus blood flow to the aneurysm may become reestablished. Additionally, not all aneurysms are suitable for coiling: (1) wide-necked aneurysms require a support scaffolding (usually a stent) as a. structural support to prevent prolapse of the coil bolus into the blood vessel; (2) aneurysms that are located in the distal reaches of the neurovasculature may lie beyond the reach of current microcatheter sizing; and, (3) microcatheters filled with embolic coils are not always flexible enough to navigate the highly tortuous and fragile anatomy of neurovascular blood vessels. As experience with coiling grows, the indications and pitfalls continue to be refined. Endovascular and coil technology continue to improve: endovascular adjuncts, such as intracranial stents, are now available to assist in coiling procedures; the original platinum microcoil has been refined with ever-improving features such as biological coating and microengineering for efficiency in deployment.

More recently, endovascular devices alternative to coils have begun to open further options for the treatment of aneurysms. Blood flow diversion without coils may provide a less expensive, more efficient, and more adaptive means for the treatment of aneurysms. Nickel-titanium-based (NiTi) flow diversion structures provide further options for physicians and patients. At present, laser cut hypotube or braided wire form the structures from which flow diverters are made. Laser cut hypotubes require complex manufacturing and have limitations in the degree of expansion deformation that they can tolerate. Alternately, braided wire forms are much less complicated to manufacture, can tolerate substantial expansion deformation, but offer very limited control of structural porosity due to the localized unconstrained movement allowable between wires that are not mechanically bound together.

Therefore, a substantial need exists to increase minimally invasive and cost-effective solutions to improve intracranial access using systems and methods to control the risk and effects of hemorrhagic stroke through means of very small, highly capable, and reliably producible interventional tools and implants.

Some aspects of the present disclosure provide the means and the methods for treating cerebral aneurysms via catheter-based, minimally invasive interventional systems that place a blood flow occluding implant into the aneurysm sac.

In some embodiments of the present disclosure the implant for treating an aneurysm is a blood flow diverter (e.g., occluder) comprised at least in part of thin film NiTi. The NiTi material may be in the martensitic (shape memory) state, the austenitic (superelastic) state, a mixture of both, or may be a multilayer of several film compositions. For example, a deployed NiTi implant of the present disclosure is in substantially the austenitic state in situ.

Some aspects of the present disclosure are directed toward an implant for treating an aneurysm that is a blood flow diverter (e.g., occluder) including an acceptable biocompatible metal including, but not limited to, biocompatible stainless steel, tantalum, tungsten, titanium, NiTi, platinum, or combinations or multilayers thereof.

Some implant embodiments may be comprised at least in part of NiTi thin film foils. Wherein the film is formed in a substantially planar form and then subsequently shaped into a three dimensional form prior to incorporation into a catheter.

Some implant embodiments may include a portion that conforms to the opening at the neck of an aneurysm.

Some implant embodiments may include a bottom portion that diverts blood flow away from the neck and sac of an aneurysm along with one or more additional portions that fill at least some of the sac volume of an aneurysm.

Some implant embodiments may be comprised at least in part of NiTi thin films wherein the film is formed in a partially three dimensional form and then subsequently further shaped into a final three dimensional form prior to incorporation into a catheter.

Some implant embodiments may be comprised at least in part of NiTi thin films wherein the film is formed in a substantially three dimensional form prior to incorporation into a catheter.

Some embodiments may be comprised at least in part of NiTi thin films wherein the film may include regularly repeating patterns of meshed structures. For example, a meshed structure may be formed from smaller identical sub elements each having a substantially uniform pore size and/or shape with substantially uniform spacing between pores. The sub elements can be arrayed in a regular connected pattern to form a larger mesh. The meshed structures may be any pattern such as shown in FIG. 1B, that optimizes the film's ability to expand from a highly compressed or wrapped state such as when loaded into a small diameter catheter to a substantially expanded state when released from a catheter into the vasculature While minimizing the degree of localized stress and strain experienced by elements of the mesh so as not to create localized stress concentration points.

Some embodiments may be comprised at least in part of NiTi thin films wherein the film may include a regularly repeating pattern of meshed structures. The meshed structures may be any pattern porosity that optimizes the occlusive performance of the structure.

Some embodiments may include one or more elements of thin film NiTi attached to a support structure, such as a guide wire or guide coil, that is utilized to interface with the catheter insertion mechanism for loading and release of the device and also to position the thin film elements in the aneurysm.

Some embodiments may include one or more elements of thin film TiNi attached to a support structure, such as a guide wire or guide coil, and may also include other laser cut hypotube or braided wire elements attached either before or after shaping to provide added structural support.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

Figure 1A:
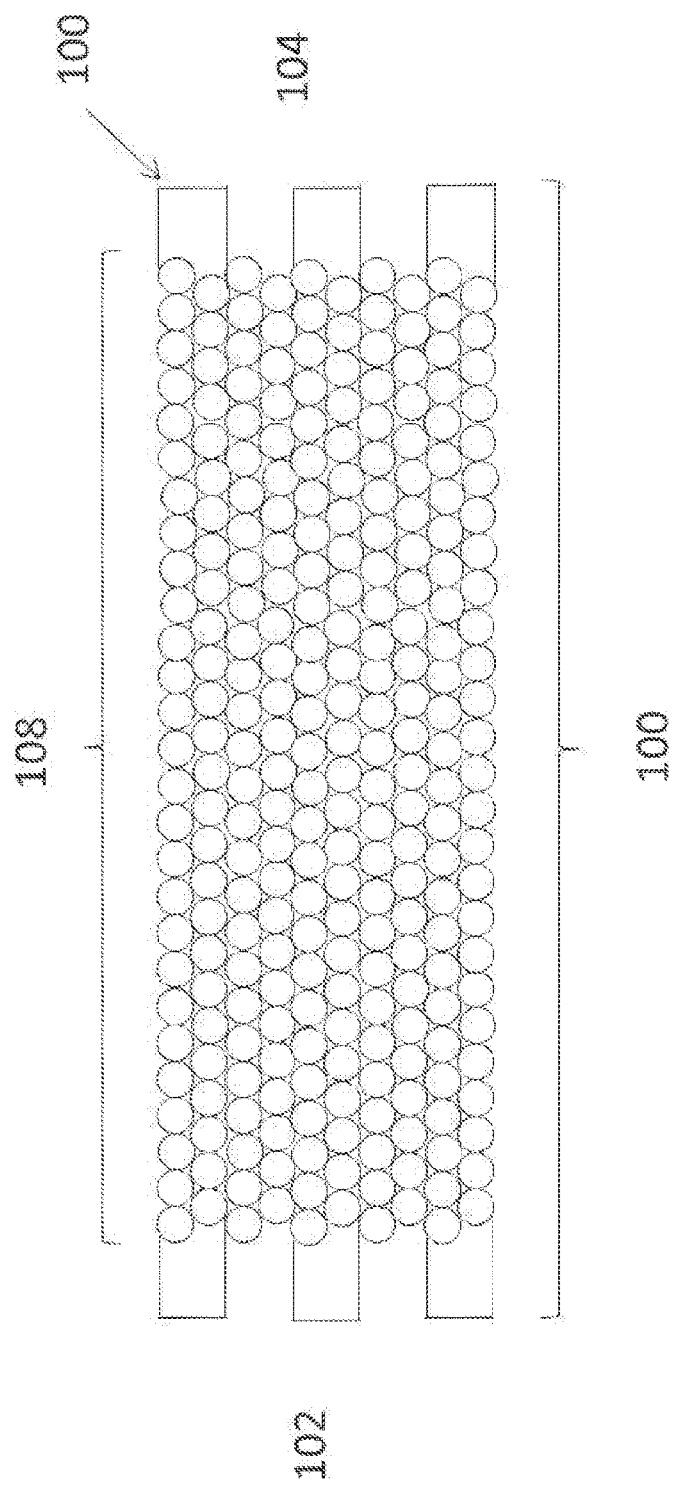
FIG. 1A shows a thin film component of an implant in a planar state.

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

DETAILED DESCRIPTION

As has been previously explained herein, there remains a need for further advancement in minimally invasive interventional treatment of cerebral aneurysms. The tortuous anatomy, small vessel diameter, and uniquely delicate anatomy of the neurovasculature provides for a particularly challenging set of constraints in which an interventional system must operate. There is little room for error given that even the smallest unintended consequences of an error often result in significant negative consequences for a patient.

Access to more distally located targets becomes limited by the size and stiffness of catheter working end which in turn may be limited by the physical aspects of the implant contained therein. A solution to this problem of limitation is to provide an implant structure that provides the simultaneous abilities of compressing to a very small diameter, below 0.027 inches or smaller, while remaining flexible in its compressed state, and then being able to expand to fixate in the interior of the aneurysm and perform safely in situ.

The present application is directed toward an implant configured to be compressed to comply with the inner diameter of the delivery system. The implant includes at least one thin film component that may be carried on a rigid, semi-rigid, or completely flexible spine system (also referred to herein as a support structure, guide structure, or guidewire). The implant includes a biocompatible material, such as NiTi wire, (Pt) platinum, (Ta) tantalum, medical grade stainless steel or any other long term implant materials.

Blood flow diversion does not require an absolutely solid surface in order to be effective. The ideal result is to provide a structure that is supple enough to avoid placing harmful pressure on the inner wall of the aneurysm sac while occluding blood flow within the sac, and also diverting blood flow back into the healthy normal pathways of the native vessel(s), and while having enough mechanical strength to safely fix in place, thus enabling the human body's natural endothelization, or clotting, to clot and seal off the disproportional wall section from the primary vessel.

For example, the thin-film component may be a fine mesh where the porosity of the mesh (e.g., open area of each pore) may range from about, 50 microns to about 1500 microns, for example about 100 microns to about 1000 microns, e.g., between about 100 microns and about 200 microns, between about 150 microns to about 250 microns, between about 200 microns to about 300 microns, between about 250 microns to about 350 microns, between about 300 microns to about 400 microns, between about 350 microns to about 450 microns, between about 400 microns to about 500 microns, between about 450 microns to about 550 microns, between about 500 microns to about 600 microns, between about 550 microns and about 650 microns, between about 600 microns and about 700 microns, between about 650 microns and about 750 microns, between about 700 microns and about 800 microns, between about 750 microns and about 850 microns, between about 800 microns and about 900 microns, between about 850 microns and about 950 microns, or between about 900 microns and about 1000 microns. Each of the thin film components described herein can include a mesh structure for blood flow diversion such that the mesh is of a substantially uniform porosity in the two-dimensional configuration and in the three-dimensional configuration.

Currently, meshes for blood flow diversion or occlusion are constructed from braided NiTi wire. However, a braided structure inherently allows the individual wires of the braid to move past one another such that the unit cells formed by individual braided strands are inconsistent (uncontrolled) in size due to deformations that naturally occur during shaping and/or handling prior to deployment. Additionally, as layers of wire stack up in a compressed and catheterized braided implant, stiffness develops that may lead to limitations in distal vascular access and/or further localized deformations of an implant's braided unit cells. These problems may be improved by creating a mesh structure from a monolithic material which will maintain the designed Shapes of any sub elements and which may include any medical grade material (metal, polymer, etc.) that is suitable for meeting the competing criteria previously described. One particular material is thin film NiTi which has been formed in a film-like thickness and patterned to have a mesh structure therein. The thin film may further be created by using film deposition and patterning processes.

Moreover, intraluminal devices such as stents require aggressive antiplatelet therapy and are associated with higher thromboembolic (TE) complication rates. Intravascular flow disrupters (IFD) are currently braided-wire devices designed to achieve flow disruption at the aneurysm neck without placing material in the parent vessel and without the need of antiplatelet therapy.

Better system performance may be achieved by producing IFDs made from NiTi thin films. As opposed to a braided structure, a thin film structure may be patterned such that the mesh is either symmetrically repetitive or otherwise preferentially patterned in an asymmetric way to provide for example surface performance optimization for a three dimensional shape with differing characteristics for the portion of the structure against the wall of the aneurysm sac versus the portion in contact with the parent artery, and diverting blood flow. One or more of these thin film features can be applied to any of the implant embodiments described herein.

The thin film components of the implant described herein can be formed from a continuous or monolithic sheet (e.g., thin film layer). The continuous or monolithic sheet can have a substantially uniform thickness and/or substantially uniform porosity in the substantially planar and three-dimensional configurations or in the compressed and uncompressed configurations. The thickness can be less than or equal to 0.005 inches, less than or equal to 0.003 inches, less than or equal to 0.002 inches, or less than or equal to 0.001 inches.

The thin film components of the implant can be patterned with a structural mesh that maintains substantially uniform porosity (e.g., amount of open area in a given area) in the compressed and uncompressed configurations. The implant's initial configuration, which may be a substantially flat or planar configuration, can include rounded, circular, elliptical, cone, and other polygonal segments. In any of the implant shape variants, there may be reinforcing portions with no porosity. The reinforcing portions may extend at least partially or entirely around a perimeter of the implant. The reinforcing portion may extend at least partially or entirely across a width or length of the implant (e.g., similar to struts). The reinforcing portions may include a same thickness as the porous or mesh portions of the implant. In addition to thin film mechanical properties such as material phase and phase transition temperature, residual strain, and mesh structural pattern, further mechanical stiffness may be derived from film thickness from layering of two or more thin film layers, and from stiffeners such as pleats or spines and the like that are formed by modifying the initial planar configuration by bending or shaping or the like into more complex 3D configurations.

The thin film components of the implant can be shape set to achieve the designated configuration so that when released into the treatment site it shall optimally fill the aneurysm and fill, block, or shield the neck transition (primary artery to aneurysm void from the same vessel wall)

to the aneurysm space. In the three-dimensional configuration, the implant has sufficient structural support to maintain its shape in a fluid pressure environment equivalent or greater to the level of high blood pressure (e.g., 3/2 psig; similar to diastolic/systolic in mm of HG for high blood pressure).

The complete occluder assembly may include one or more thin film mesh components plus one or more support structures that may be wire, coil, or laser cut material. The components may be shape set individually prior to integration or the assembly may also be shape set as a complete or partially complete unit.

Corrosion resistance and biocompatibility may be enhanced by placement of an inert micro layer of metallic or non-metallic material at an atomic level, or greater thickness, to ensure of a surface passivation that is robust and can resist corrosion or leach ions into the blood system. The final outer surface may have a final surface finish of material that will be inert to the body and resist corrosion by placing an atomic layer of (Ti) titanium, (Pt) Platinum, (Pd) palladium, (Ir) iridium, (Au) Gold, (Ta) tantalum, or other biocompatible metals or may be passivated by the formation of a surface titanium oxide layer. Stainless steel thin films shall be consistent with the medical grade ISO standard requirements of 316, 316L, 316 LVM, 17/7 and any other long term implant materials.

In some embodiments, the mesh of an implant is substantially or predominantly in the austenitic phase so as to provide the best superelasticity and load carrying strength. The greater the difference between body temperature and the temperature at which an implant and mesh transform into the austenitic stage, the "Af temperature", the greater the stiffness. However, with increased stiffness come tradeoffs in fatigue resistance. Therefore, an optimized structure of mesh offers a good combination of thermomechanical properties and mesh geometry to allow for localized distortions during deployment and release in situ, during manufacturing manipulations, and during catheterized delivery through tortuous vasculature. Af temperatures may range from 10 degrees Celsius to 37 degrees Celsius. The film thickness can be in a range from 1 micron to 50 microns, for example from about 6 microns to about 12 microns, wherein the thickness is a factor in the outward force and the controlled resistance to compression forces from the blood vessel.

The implants described herein can be compressed by wrapping the implant around the support structure. For example as shown in FIG. 3B, the implant may be compressed by wrapping one portion of the thin film component over another portion of the thin film component to form an overall conical shape. By increasing the amount or number of turns of overlap, the cone can be loaded into a small diameter catheter for insertion into the vasculature. After release from catheter, the cone can expand to a larger diameter to match the size of the target aneurysm.

Any of the embodiments described herein may include radiopaque marker bands that can be made from tantalum, titanium or precious metal and placed on the occluder at any specific location where an eyelet or nodule is formed by the thin film process or to a support structure, such as a straight wire or wire having a coil portion, of the complete device. The marker may be crimped, swaged, fused or adhered to the eyelet or the frame based on the optimum location for the identification of placement of the occluder in the body by x-ray (fluoroscopy). The marker may also be plated onto the specific location or dip plated to ensure the patency of a specific area of the Occluder is visible under fluoroscopy. Alternatively, radiopacity may be achieved by adding high brightness metals either as a surface coating or by inclusion into a multilayer structure in such amounts that do not compromise the shaping of the material into desired 3 dimensional forms or its mechanical robustness as required for successful deployment.

The occluder shall be sized based on the fluoroscope sizing of the aneurysm determined by the neurovascular surgeon. The catheter assembly shall be preloaded with the specific occluder and sterilized by means of gamma, e-beam or ETO, without impacting the overall device capability for a one-time-use and achieving the trackability to the specific location without any friability to the delivery system or the occluder. Once in position, confirmed by the neurovascular surgeon by fluoroscopy, the center delivery wire can be manipulated by torque and axial pushing to ensure the delivery system tip is at the neck of the aneurysm area. The release shall be completed by moving the inner delivery wire distally, or by moving the outer sheath proximally or by both at the same time. The occluder shall change from the configured loaded shape to the final configured shape partially as it exits the sheathed state but will achieve its final shape once fully released from the delivery system.

Figure 1B:
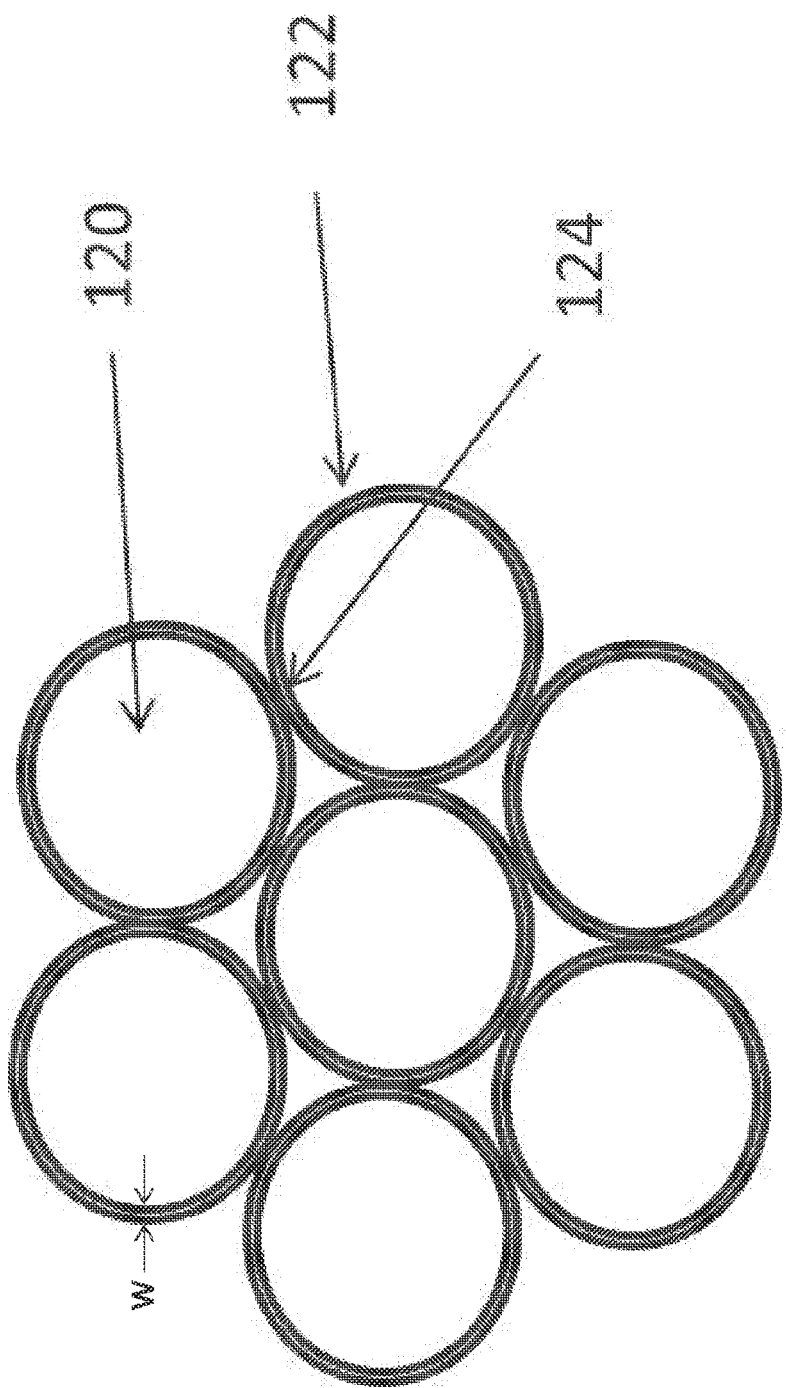
FIG. 1B shows a partial, enlarged view of the implant shown in FIG. 1A.

FIGS. 1A and 1B show an embodiment of a thin film component 100 of an occlusion device in its starting two-dimensional configuration (see FIG. 1A). In some configurations, this element can be constructed from thin-film nitinol.

The occlusion device includes a mesh structure having a porosity 120 with a substantially uniform or uniform pore size (see FIG. 1B). Any single pore size can be within at least about 5% of a pore size of any other pore or the mean pore size. The space between any two pores can be within at least about 5% of the space between any other two pores or the mean spacing between pores for the entire thin film component. The size of the perforation holes and the dimensions of the supporting mesh are chosen to maximize the occlusive performance in the device while maintaining sufficient structural strength to enable handling and deployment of the device without tearing.

In the starting 2D configuration, the thin film component 100 is in a flat, planar configuration. At rest, the thin film component 100 has a substantially uniform or uniform thickness, for example, a thickness of the thin film element 100 is at least about 0.2 mils and/or less than or equal to about 2.0 mils, such as between about 0.5 mils to about 1.5 mils or between about 1.0 mils to about 2.0 mils.

As shown in FIG. 1A, the thin film element 100 extends from a first end portion 102 to a second end portion 104. While the main portion 108 of the element is formed of an array of mesh structures, it may also include additional tabs or similar structures, for example by incorporating end tabs 106 as shown in FIG. 1A.

FIG. 1B shows a close-up of a mesh structure showing the detail of the sub elements. Any of the embodiments described herein may include this structure of sub elements. The porosity 120 is formed from interconnected rings 122. The pore opening dimension is chosen to optimize the occlusive performance of the element in situ, where the porosity of the mesh (e.g., open area of each pore) may range from about, 50 microns to about 1500 microns, for example about 100 microns to about 1000 microns. In the embodiment shown, each ring 122 is circular in shape although other shapes can be utilized including but not limited to ovals or polygons.

The cross sectional dimensions of the solid portions the rings 122 have a width and a thickness. The width is determined by the thin film patterning process used to delineate the layout of the structure, while the film thickness is determined by the amount of material deposited during the thin film deposition process. The width w of the solid annulus of the rings can be at least about 1 micron and/or less than or equal to about 100 microns, for example from 1 to 20 microns or 5 to 10 microns. The thickness (into the page in FIG. 1B) can be at least about 0.2 mils and/or less than or equal to about 2.0 mils, such as between about 0.5 mils to about 1.5 mils or between about 1.0 mils to about 2.0 mils.

In order to create a mesh, each individual ring 122 is connected on its outer diameter to surrounding rings at attachment points 124 to create a close packed array.

Figure 1C:
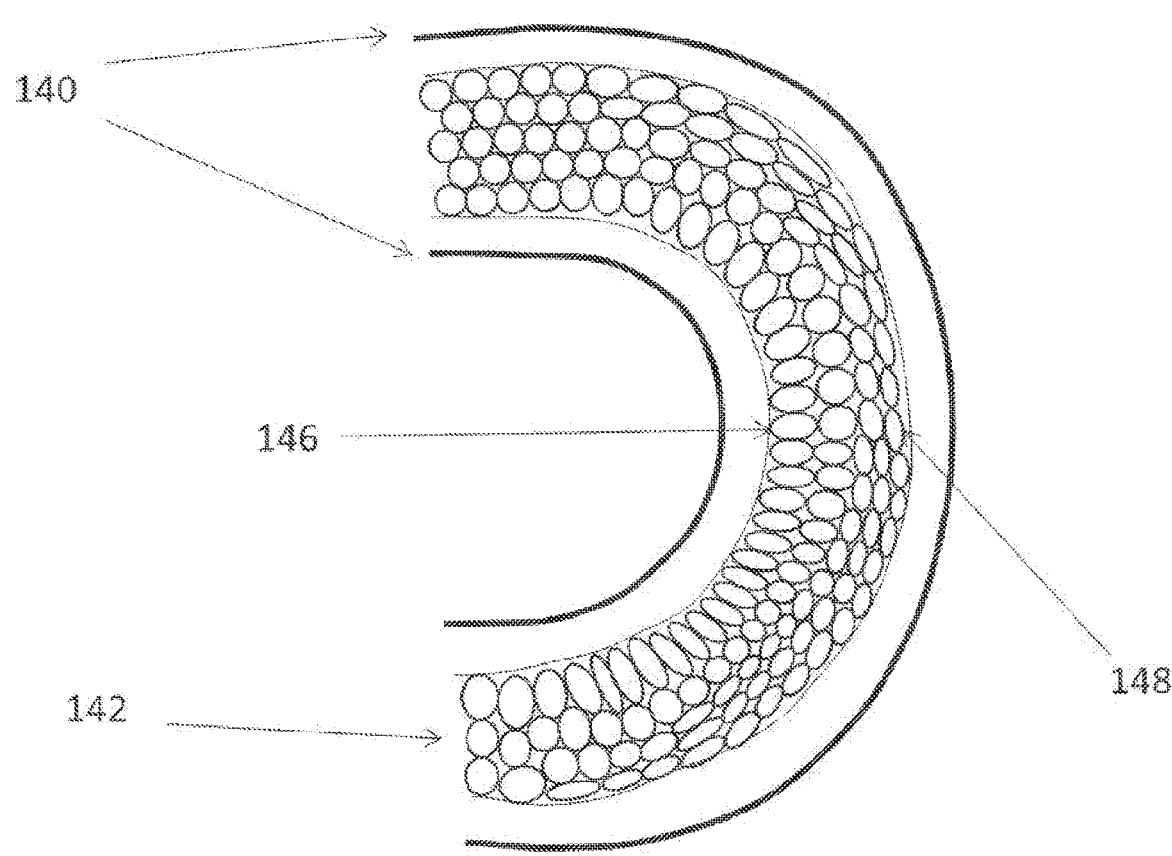
FIG. 1C shows an implant as contained in a curved catheter section.

For successful deployment into the aneurysm, the implant as constrained in the catheter must be capable of navigating the tortuous anatomy of the vasculature system without damage or irreversible distortion of the components. As shown in FIGS. 1A and 1B a mesh of rings is utilized. The ring structure is flexible to distortions in any direction, since the circular rings have no preferred axis and have uniform stiffness in all directions. As an example, as shown in FIG. 1C, if catheter 140 needs to be pushed through a curved region in the vasculature, the regions of the device that transit through the outer radius 148 of the bend must expand along the axis of the bending, relative to their shape 142 in a straight segment, and the regions 146 on the inner radius must contract. Since the catheter may have to move through multiple bends in varying directions to reach the deployment location, it is desired that the device be flexible for arbitrarily orientated stretching of the mesh elements.

Figure 2A:
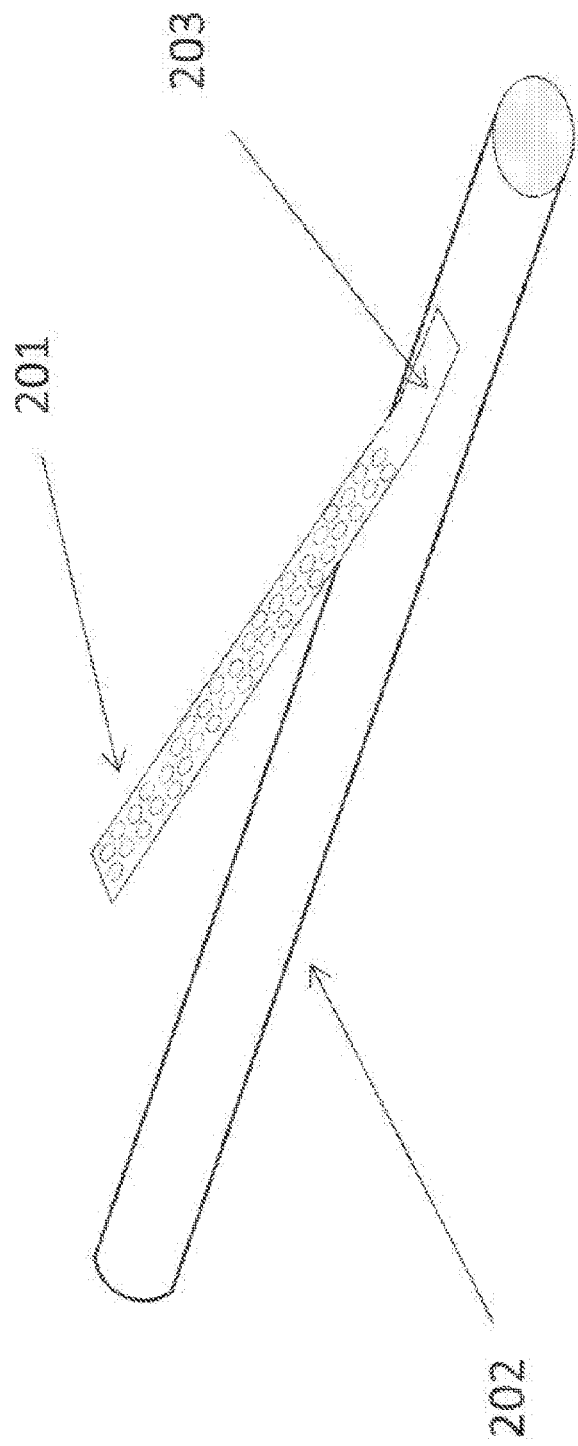
FIG. 2A shows an implant with the thin film component of FIG. 1A attached to a support structure.

FIG. 2A shows an implant with a thin film component 201 attached to a support structure 202 at attachment location 203. The thin film component 201 can extend radially outward in at least one direction from the support structure 202. The thin film component can include any of the features of thin film element 100. The support structure 202 may be a straight wire or an embolic coil. The method of attachment may be adhesive, welding, soldering, or any other means and may utilize tabs, grommets, or other features delineated in the thin film.

Figure 2B:
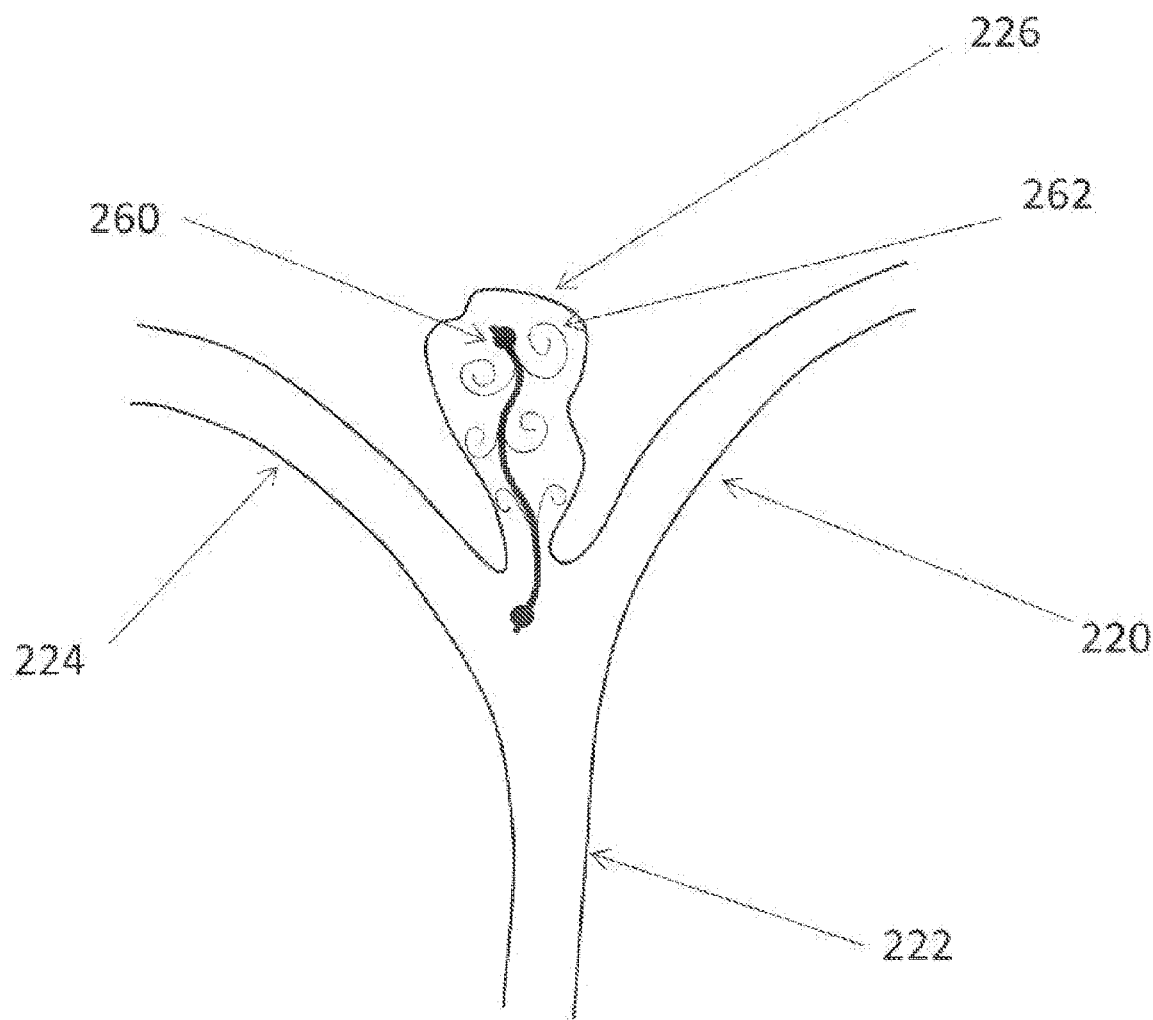
FIG. 2B shows the implant of FIG. 2A deployed in an aneurysm.
Figure 2C:
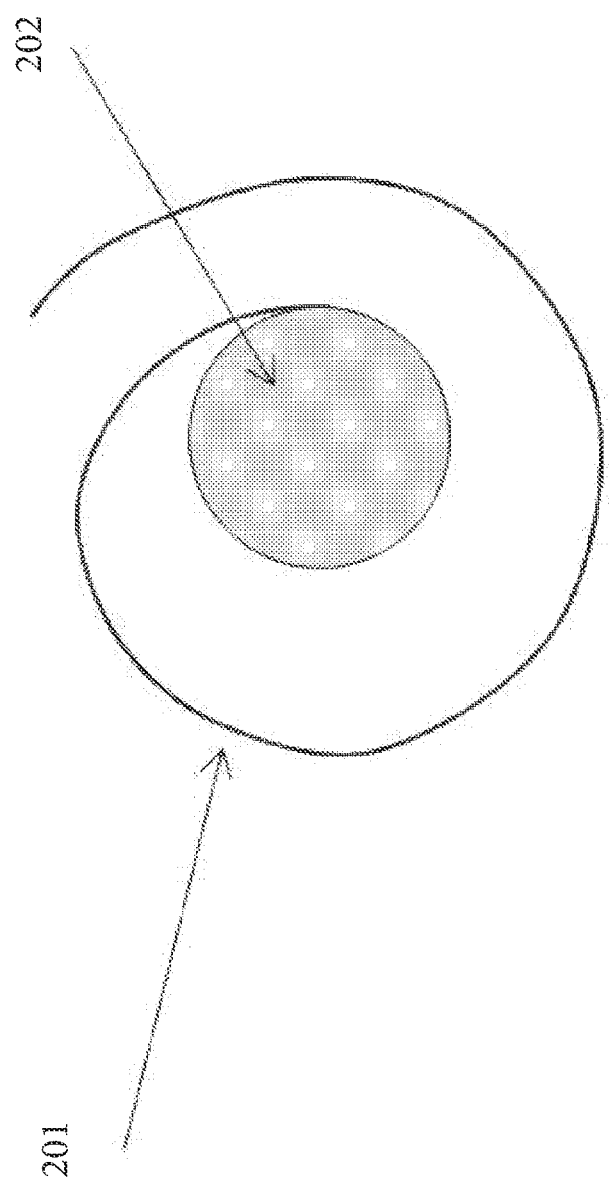
FIG. 2C shows an end view of the thin film component of FIG. 1A wrapped for loading into a catheter assembly.

FIG. 2B shows an embodiment where multiple thin film component 262 have been shape set into 3D forms prior to attachment to the support structure 202. FIG. 2C shows an end view of the implant that shows an example of how a thin film component 201 can be wrapped around a support structure 202 for loading into a catheter tube. When released into the aneurysm, the wrapped thin film components 201 will unfold into the 3D shape set configuration as in FIG. 2B. In some embodiments, a full length of the support structure is released. In some embodiments, the length of the support structure being released is customizable in situ.

FIG. 2B shows an embodiment of a deployed implant where multiple thin film components 262 have been shape set into 3D forms prior to attachment to the support structure 260 where 226 is an aneurysm located in a y-junction formed by blood vessel segments 220, 222, and 224.

Current embolic coiling treatments are based on the ability to accurately place enough length of coil, or multiple coils, to fill the volume of the aneurysm to a high enough packing density that blood flow into and out of the aneurysm is reduced to a level that thrombosis can occur. Typical volumetric fill factors are less than 40%. Since the detailed packing of the coil into the aneurysm is largely random in nature and can vary from patient to patient, it is difficult for the neurosurgeon to determine in advance or even during the implant procedure exactly what length of coil will be required. Not enough coil length will result in insufficient packing density, and too long a length of coil can place higher radial pressure on the walls of the aneurysm, risking rupture, or leave a portion of coil protruding into the parent blood vessel, necessitating additional implants of stent like elements into the vessel.

By adding additional thin film components onto a support structure, as indicated above, the occlusive surface area per unit length of the support structure is enhanced relative to a plain coil, reducing the overall length required to produce thrombosis and thus simplifying the procedure. Furthermore the thin film components can be constructed with uniform and optimally sized pore opening for enhanced clotting characteristics.

Figure 3A:
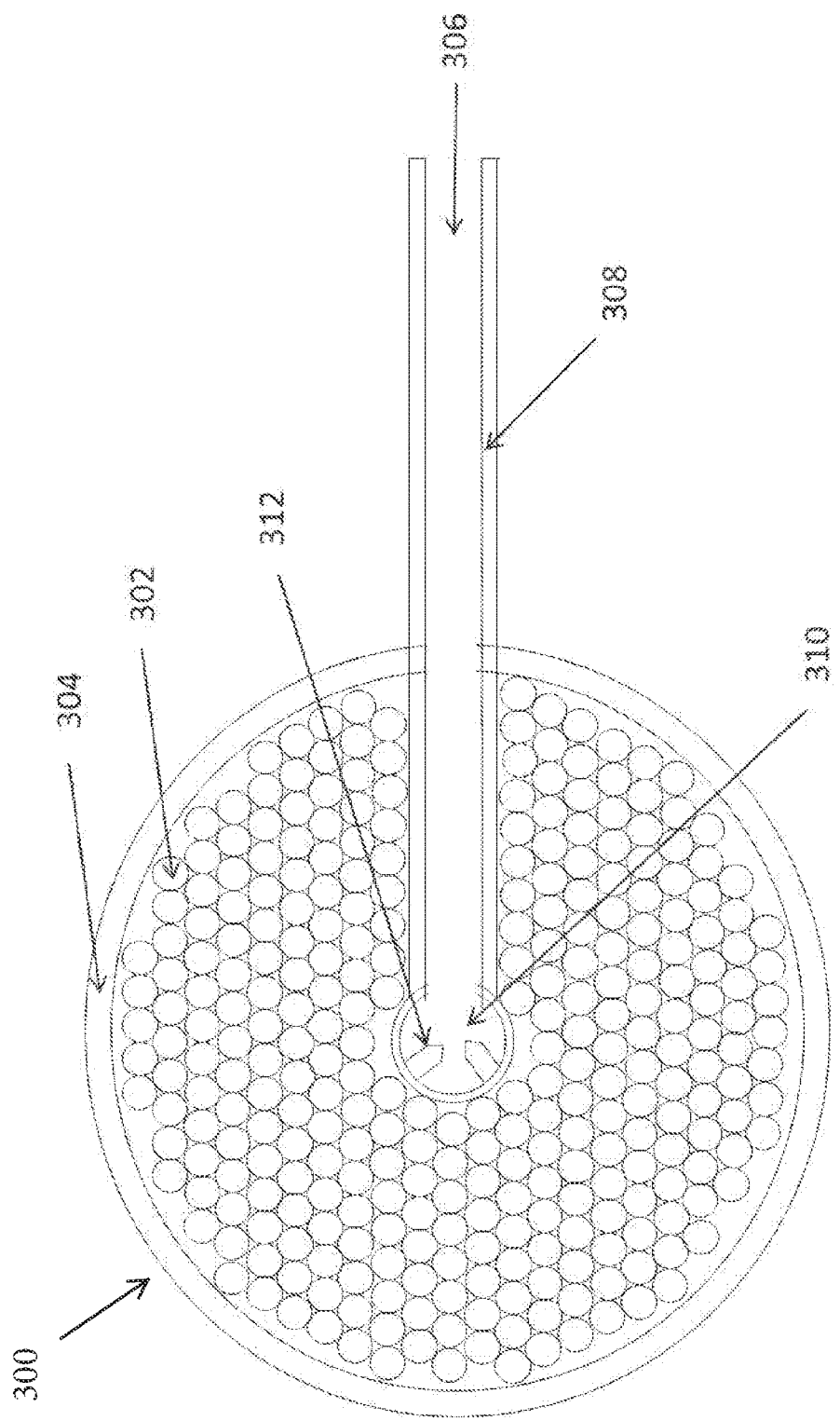
FIG. 3A shows another embodiment of a thin film component of an implant in a planar state.
Figure 3B:
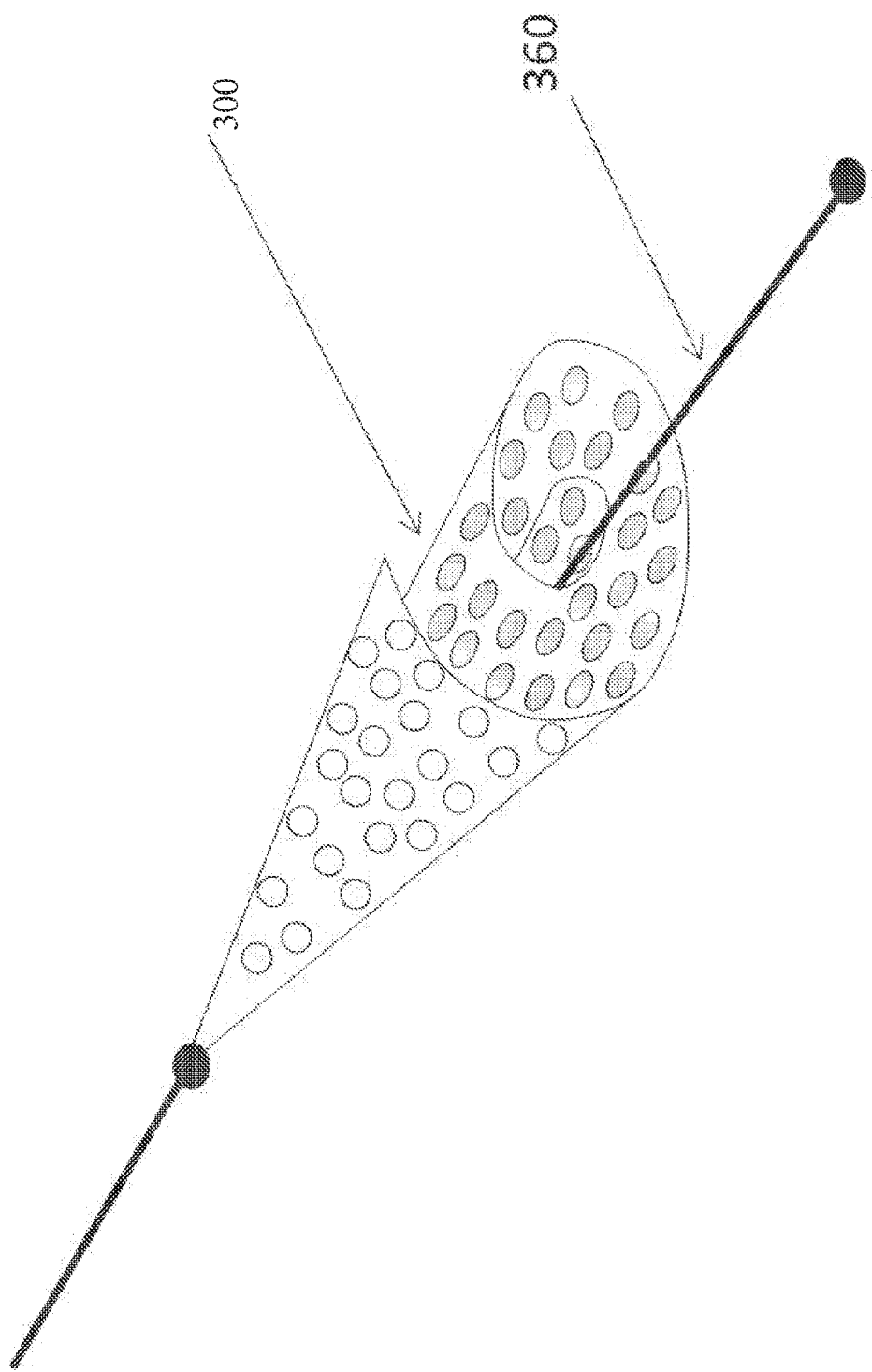
FIG. 3B shows the thin film component of FIG. 3A wrapped for catheter loading.

FIGS. 3A and 3B show another embodiment. FIG. 3A shows a disc of thin film material 300 in its 2D configuration that has an area of uniform porosity 302 surrounded by a reinforcing portion or solid border 304 with no porosity. The disc 300 can include any features of the thin film element 100. For example, the disc 300 can have a slot 306 with tabs 308. At the center of the disc is a hole 310 that may have additional tabs 312. One or more thin film components 300 can be wrapped around a support structure 360, such as a guide wire or coil, as shown in FIG. 39. The guide wire is inserted through the center hole 310 and may be attached in position using tabs 312 or any of the other attachment methods of attachment as described above with respect to FIG. 2A. The slot 306 enables the disc 300 to be wrapped as shown in FIG. 3B with overlapping portions and into a diameter consistent with catheter loading with minimal folding of the film. After release, the disc 300 can at least partially expand to fill the aneurysm, for example as shown in FIG. 4B.

Figure 4A:
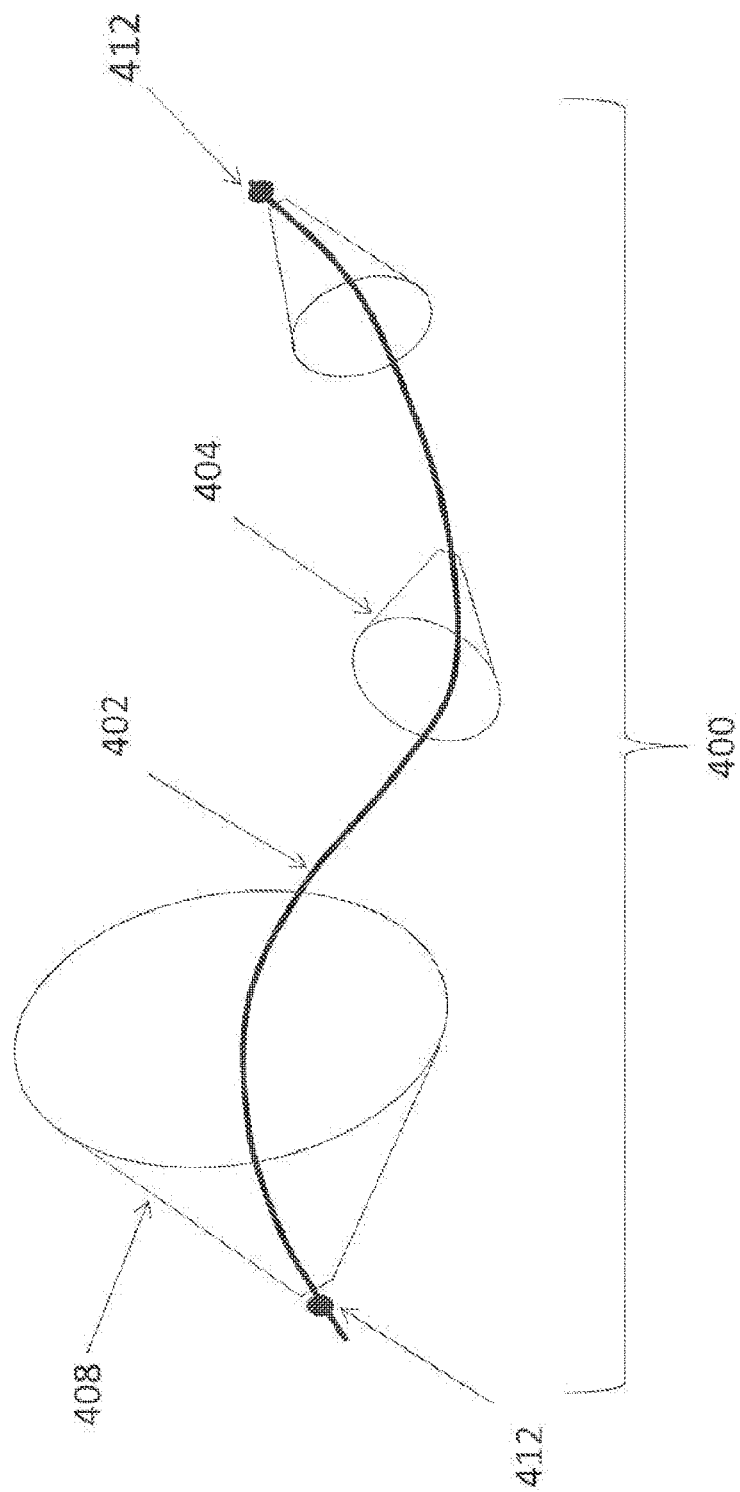
FIG. 4A shows an implant with the thin film component of FIG. 4A attached to a support structure.
Figure 4B:
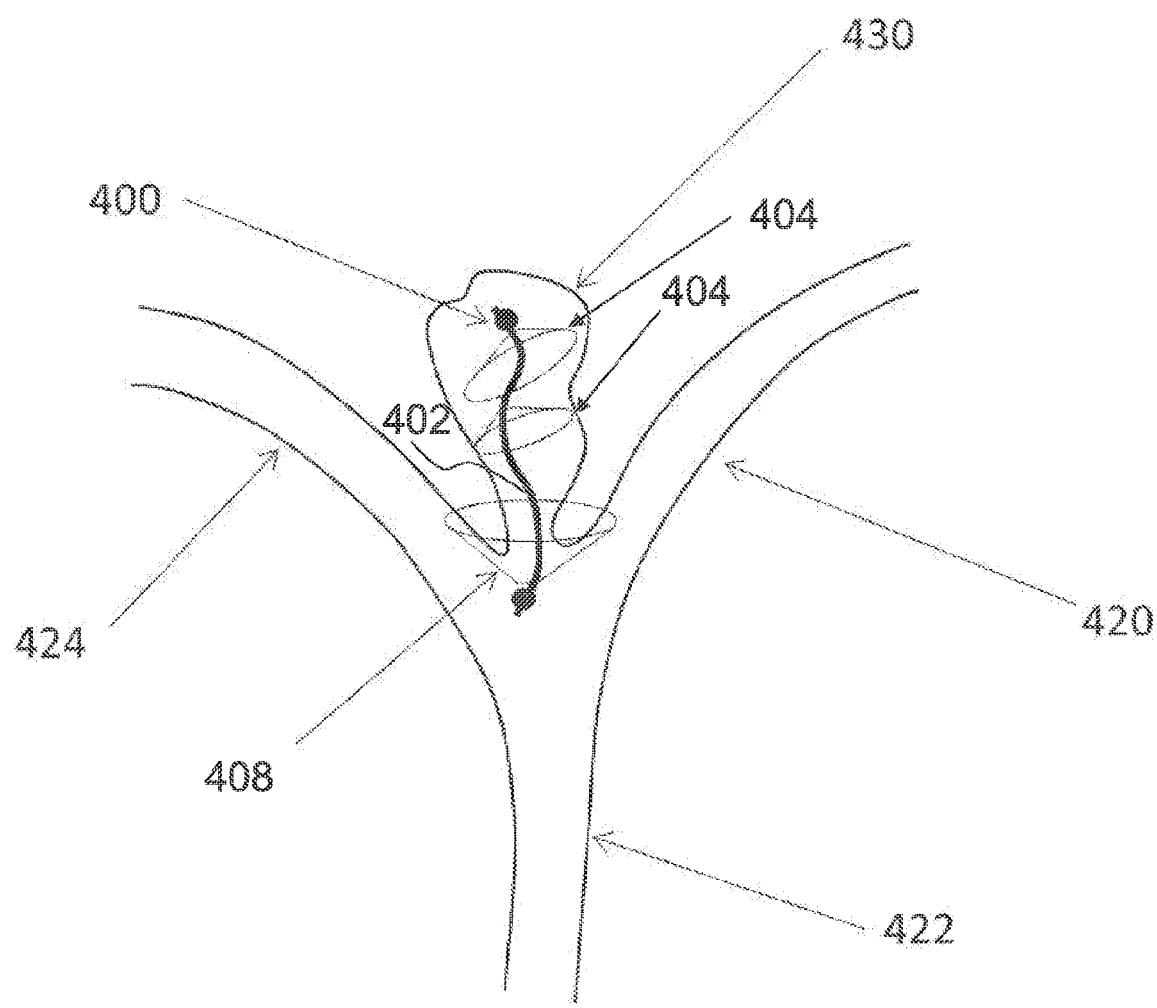
FIG. 4B shows the implant of FIG. 4A deployed in an aneurysm.

FIGS. 4A and 4B show how the thin film discs 300 are integrated into an implant assembly 400. One or more thin film discs 404 can be attached to a support structure 402 using any of the methods described above. The thin film discs 404 can include any of the features of thin film element 100 or thin film discs 300. The thin film discs 404 are of diameter slightly larger than the diameter of the aneurysm so that when released from the catheter they will unwind to achieve a fit of their outer edges to the wall of the aneurysm. Each of the thin film discs 404 form a conical configuration. One or more discs 404, for example two, three, or more, are attached so that an apex of each cone is oriented toward a distal end of the support structure 402 and away from the aneurysm neck (see FIG. 4B) to facilitate insertion into the aneurysm. At least one additional disc 408 with a larger diameter than the discs 404 can be attached at the proximal end of the support structure 402 and is orientated with the apex of its cone in the opposite direction to the smaller discs 404 and toward the proximal end of the support structure 402. When disc 408 exits the catheter, it will open up to a larger diameter than the neck of the aneurysm effectively diverting blood flow at the neck. This is shown in FIG. 4B where 430 is an aneurysm located in a y-junction formed by blood vessel segments 420, 422, and 424. Implant assembly 400 is shown as inserted into the aneurysm with disc 408 blocking the neck.

In addition to the thin film discs, guide wire 402 may also have x-ray observable clips or similar elements attached to one or both ends and may also have attached balls 412 for detachment from the catheter push rod.

Figure 5:
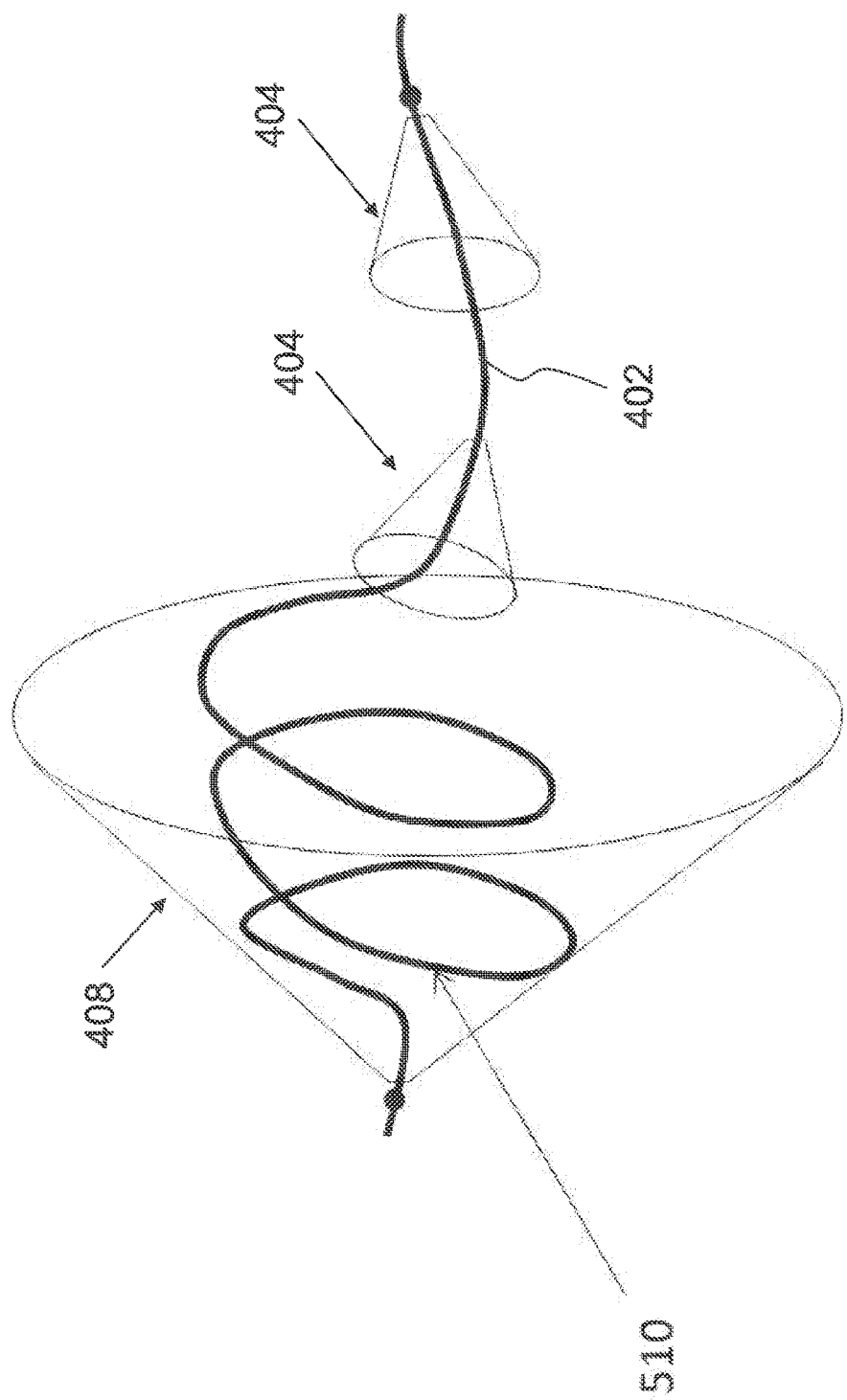
FIG. 5 shows another implant with the thin film component of FIG. 4A with a support structure having a coiled configuration.

FIG. 5 shows an additional embodiment of the assembly of type 400 that includes one or more thin film discs 404 and a spiral shaped portion 510 that has been shape set into the guide wire 402. This region can be pulled straight prior to insertion into the catheter to provide additional length inside the constraint of the catheter to reduce any overlapping between discs 404 and 408 to facilitate opening up of the cones during the implanting process. It also functions to provide a pulling force to seat disc 408 onto the opening neck of the aneurysm.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Although certain embodiments and examples have been described herein, it will be understood by those skilled in the art that many aspects of the delivery systems shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

The terms "approximately," "about," and "substantially" as used herein represent an amount close to the stated amount that still performs a desired function or achieves a desired result. For example, the terms "approximately", "about", and "substantially" may refer to an amount that is within less than 10% of the stated amount. As another example, in certain embodiments, the terms "generally parallel" and "substantially parallel" refer to a value, amount, or characteristic that departs from exactly parallel by less than or equal to 15 degrees.

EXAMPLE EMBODIMENTS

The following example embodiments identify some possible permutations of combinations of features disclosed herein, although other permutations of combinations of features are also possible.

1. A deployable occlusion device for filling an aneurysm, the occlusion device comprising:
   a support structure comprising a wire; and
   a mesh component comprising a porosity, the mesh component comprising a first end portion and a second end portion, the first end portion being attached to the support structure and the second end portion being a free end, the mesh component extending radially outward from the support structure.

2. The occlusion device of Embodiment 1, wherein the mesh component is configured to transition between a compressed state and an uncompressed state, the mesh component forming a coil in the uncompressed state.

3. The occlusion device of Embodiment 2, wherein in the compressed state, the mesh component is wrapped around the support structure.

4. The occlusion device of any one of Embodiments 1 to 3, wherein the support structure comprises a coiled region.

5. The occlusion device of any one of Embodiments 1 to 4, wherein the support structure comprises a straight region.

6. The occlusion device of any one of Embodiments 1 to 5, wherein the mesh component is attached to the support structure by adhesive, welding, or soldering.

7. The occlusion device of any one of Embodiments 1 to 5, wherein the mesh component is mechanically attached to the support structure.

8. The occlusion device of Embodiment 7, wherein the mesh component has at least one tab for engaging the support structure.

9. The occlusion device of any one of Embodiments 1 to 8, wherein the mesh component is monolithic.

10. The occlusion device of any one of Embodiments 1 to 9, wherein the mesh component comprises a wall thickness of no more than 0.002 inches.

11. The occlusion device of any one of Embodiments 1 to 10, wherein the mesh component has a substantially uniform pore size.

12. The occlusion device of any one of Embodiments 1 to 11, wherein the mesh component has substantially uniform porosity.

13. The occlusion device of any one of Embodiments 1 to 12, wherein the first end portion does not have porosity.

14. The occlusion device of any one of Embodiments 1 to 13, further comprising a plurality of mesh components, each mesh component extending from the support structure.

15. A deployable device for filling an aneurysm, the occlusion device comprising:
   a support structure comprising a wire, the support structure comprising a proximal end and a distal end; and
   a plurality of mesh components longitudinally spaced along the support structure, each mesh component comprising a porosity, the mesh component being configured to transition between a compressed state and an uncompressed state.

16. The occlusion device of Embodiment 15, wherein each mesh component forms a conical shape in the uncompressed state so that each mesh component comprises an apex and an open end, the apex of each mesh component being attached to the support structure.

17. The occlusion device of Embodiment 15 or 16, wherein the support structure comprises a coiled region.

18. The occlusion device of any one of Embodiments 15 to 17, wherein the support structure comprises a straight region.

19. The occlusion device of any one of Embodiments 15 to 18, wherein the plurality of mesh components comprises a first mesh component and a second mesh component.

20. The occlusion device of Embodiment 19, wherein the open end of the second mesh component has a larger diameter than the open end of the first mesh component.

21. The occlusion device of Embodiment 19 or 20, wherein the apex of the first mesh component is oriented in an opposite direction from the apex of the second mesh component.

22. The occlusion device of any one of Embodiments 19 to 21, wherein the apex of the second component is configured to be positioned in a neck of the aneurysm.

23. The occlusion device of any one of Embodiments 15 to 22, wherein each mesh component is attached to the support structure by adhesive, welding, or soldering.

24. The occlusion device of any one of Embodiments 15 to 23, wherein each mesh component is mechanically attached to the support structure.

25. The occlusion device of Embodiment 24, wherein each component has at least one tab for engaging the support structure.

26. The occlusion device of any one of Embodiments 15 to 25, wherein each mesh component is monolithic.

27. The occlusion device of any one of Embodiments 15 to 26, wherein each mesh component comprises a wall thickness of no more than 0.002 inches.

28. The occlusion device of any one of Embodiments 15 to 27, wherein each mesh component has a substantially uniform pore size.

29. The occlusion device of any one of Embodiments 15 to 28, wherein each mesh component has substantially uniform porosity.

30. The occlusion device of any one of Embodiments 15 to 29, wherein a peripheral edge of the open end of each mesh component has no porosity.

31. The occlusion device of any one of Embodiments 15 to 30, wherein each mesh component comprises a radially extending slot.

32. A method of deploying an occlusion device into an aneurysm, the method comprising:
advancing a delivery system carrying the occlusion device to the aneurysm;
deploying the occlusion device from the delivery system such that the occlusion device transitions from a constrained configuration to an expanded configuration, the occlusion device comprising:
a support structure; and
a mesh structure extending from the support structure; and
releasing the occlusion device from the delivery system.

33. The method of Embodiment 32, wherein advancing the delivery system comprises advancing the delivery system through a curved region in the vasculature, the curved region having an inner radius and an outer radius, a first portion of the mesh structure expanding along an axis of bending along the outer radius and a second portion of the mesh structure contracting along the axis of bending along the inner radius.

34. The method of Embodiment 32 or 33, wherein deploying the occlusion device comprising positioning a bottom portion of the occlusion device at a neck portion of the aneurysm and a remaining portion of the occlusion device within a sac volume of the aneurysm.

What is claimed is:

1. An implantable occlusion device for filling an aneurysm, the occlusion device comprising:
a support structure configured to be implanted in the aneurysm, the support structure comprising a wire; and
a plurality of mesh components, each mesh component comprising a porosity, each mesh component comprising a first end portion and a second end portion, the first end portion being attached to the support structure and the second end portion being a free end, each mesh component extending from the support structure,
wherein each mesh component is configured to transition between a compressed state and an uncompressed state,
wherein each mesh component comprises a disc having a slot, and
wherein in the compressed state, each mesh component is wrapped around the support structure, the slot enabling the disc to be wrapped around the support structure with overlapping portions.

2. The occlusion device of claim 1, wherein the support structure comprises a coiled region.

3. The occlusion device of claim 1, wherein the support structure comprises a straight region.

4. The occlusion device of claim 1, wherein each mesh component is attached to the support structure by adhesive, welding, or soldering.

5. The occlusion device of claim 1, wherein each mesh component is mechanically attached to the support structure.

6. The occlusion device of claim 1, wherein each mesh component is formed from a monolithic film.

7. The occlusion device of claim 1, wherein each mesh component has substantially uniform porosity.

8. The occlusion device of claim 1, wherein the disc of each mesh component has a conical shape in the uncompressed state, the conical shape comprises an apex and an open end, the apex of the disc of each mesh component being attached to the support structure.

9. The occlusion device of claim 1, wherein the plurality of mesh components comprise a first disc and a second disc, each of the first disc and the second disc having a conical shape in the uncompressed state, the conical shape comprising an apex and an open end.

10. The occlusion device of claim 9, wherein the open end of the second disc has a larger diameter than the open end of the first disc.

11. The occlusion device of claim 9, wherein the apex of the first disc is oriented in an opposite direction from the apex of the second disc.

12. The occlusion device of claim 9, wherein the apex of the second disc is configured to be positioned in a neck of the aneurysm.

13. The occlusion device of claim 1, wherein the disc comprises a center hole having at least one tab.

14. The occlusion device of claim 13, wherein each mesh component is attached to the support structure using the at least one tab.

15. A method of deploying an occlusion device into an aneurysm, the method comprising:
advancing a delivery system carrying the occlusion device to the aneurysm, the occlusion device comprising a support structure and a plurality of mesh structures extending from the support structure, the plurality of mesh structures wrapped around the support structure in a constrained configuration when loaded in the delivery system, each mesh structure having a slot enabling the mesh structure to be wrapped around the support structure with overlapping portions;

deploying the occlusion device from the delivery system and into the aneurysm, causing each of the plurality of mesh structures to unfold from the constrained configuration to an expanded configuration to enhance an occlusive surface area per unit length of the support structure; and releasing the occlusion device from the delivery system.

16. The method of claim 15, wherein the disc comprises a center hole having at least one tab.

17. The method of claim 16, wherein advancing the delivery system comprises advancing the delivery system through a curved region in the vasculature, the curved region having an inner radius and an outer radius, a first portion of each mesh structure expanding along an axis of bending along the outer radius and a second portion of each mesh structure contracting along the axis of bending along the inner radius.

18. The method of claim 16, wherein deploying the occlusion device comprising positioning a bottom portion of the occlusion device at a neck portion of the aneurysm and a remaining portion of the occlusion device within a sac volume of the aneurysm.

19. The method of claim 16, wherein in the expanded configuration, each of the plurality of mesh structures forms a conical configuration.

* * * * *

UNITED STATES PATENT AND TRADEMARK OFFICE
CERTIFICATE OF CORRECTION

| | |
|---|---|
| PATENT NO. | : 11,589,872 B2 |
| APPLICATION NO. | : 16/965919 |
| DATED | : February 28, 2023 |
| INVENTOR(S) | : Philip Mauger |

It is certified that error appears in the above-identified patent and that said Letters Patent is hereby corrected as shown below:

In the Specification

Column 1, Line 14, delete "60,000,00" and insert -- 60,000,000 --.

Column 2, Line 20, delete "a." and insert -- a --.

Column 2, Line 32, delete "Endovascualrly" and insert -- Endovascularly --.

Column 2, Line 37, delete "manner" and insert -- manner. --.

Column 2, Line 52, delete "a." and insert -- a --.

Column 3, Line 40, delete "foils. Wherein" and insert -- foils wherein --.

Column 4, Line 4, delete "While" and insert -- while --.

Column 4, Line 41, delete "of FIG. 2A" and insert -- with multiple thin film components --.

Column 6, Line 4, delete "Shapes" and insert -- shapes --.

Column 7, Line 25, delete "316 LVM," and insert -- 316LVM, --.

Column 10, Line 23, delete "39." and insert -- 3B. --.

Column 12, Line 21, delete "componentis" and insert -- component is --.

Column 13, Line 24, after "each" insert -- mesh --.

Signed and Sealed this
First Day of August, 2023

Katherine Kelly Vidal
*Director of the United States Patent and Trademark Office*

In the Claims

Column 15, Line 10, Claim 17, delete "claim 16," and insert -- claim 15, --.

Column 15, Line 18, Claim 18, delete "claim 16," and insert -- claim 15, --.

Column 15, Line 23, Claim 19, delete "claim 16," and insert -- claim 15, --.